United States Patent [19]

Frohberger et al.

[11] 4,027,032
[45] May 31, 1977

[54] COMBATING HEMINTHOSPORIUM FUNGI WITH 2-[3',5'-DIMETHYLPYRAZOLYL-(1')]-BENZIMIDAZOLE

[75] Inventors: Paul-Ernst Frohberger, Leverkusen; Walter Gauss, Cologne, both of Germany

[73] Assignee: Bayer Aktiengesellschaft, Leverkusen, Germany

[22] Filed: Oct. 30, 1975

[21] Appl. No.: 627,412

[30] Foreign Application Priority Data
Nov. 9, 1974  Germany ............................ 2453210

[52] U.S. Cl. .............................................. 424/273
[51] Int. Cl.² .......................................... A01N 9/22
[58] Field of Search .................................... 424/273

[56] References Cited

FOREIGN PATENTS OR APPLICATIONS 1,334,348  10/1973  United Kingdom

*Primary Examiner*—V. D. Turner
*Attorney, Agent, or Firm*—Burgess, Dinklage & Sprung

[57] ABSTRACT

Combating fungi of the genus Helminthosporium with the known compound 2-[3',5'-dimethylpyrazolyl-(1')]-benzimidazole of the formula

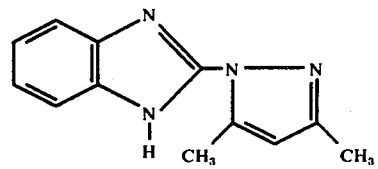

5 Claims, No Drawings

COMBATING HEMINTHOSPORIUM FUNGI WITH 2-[3',5'-DIMETHYLPYRAZOLYL-(1')]-BENZIMIDAZOLE

The present invention relates to the use, as a fungicidal agent for combating fungi of the genus Helminthosporium, of the known compound 2-[3',5'-dimethylpyrazolyl-(1')]-benzimidazole.

It has been disclosed in German Published Specification DOS 2,130,030 that 2-[pyrazolyl-(1')]-benzimidazoles generally exhibit fungicidal and bactericidal activity. However, nothing has been disclosed hitherto regarding any activity of these compounds specifically against phytopathogenic fungi of the genus Helminthosporium.

It has now been found that specifically 2-[3',5'-dimethylpyrazolyl-(1')]-benzimadzole, of the formula

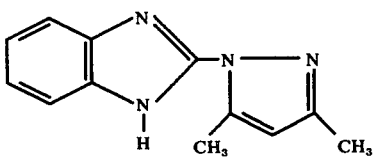

(I), has a strong fungicidal action against fungi of the genus Helminthosporium.

The present invention accordingly provides a method of combating fungi from the genus Helminthosporium, which comprises applying to such fungi, or to a habitat thereof, 2-[3',5'-dimethylpyrazolyl-(1')]-benzimidazole, alone or in admixture with a diluent or carrier.

Surprisingly, the compound which can be used according to the invention exhibits a considerable fungitoxic activity especially against species of Helminthosporium and in this respect surpasses all known compounds from the category of the 2-pyrazolyl-benzimidazoles.

The combating of phytopathogenic fungi of the genus Helminthosporium is an important problem in agriculture. Thus, the fungus *Helminthosporium gramineum*, the pathogen of stripe disease of barley, causes great losses in yield. Its successful combating therefore represents a considerable technical advance.

The compound which is to be used according to the invention is disclosed in German Published Specification DOS 2,130,030 and the corresponding British Pat. Specification No. 1,334,348. It is prepared by reaction of 2-hydrazino-benzimidazole with acetylacetone as shown hereinbelow.

As has been mentioned, the active compound which can be used according to the invention has a very good action against species of Helminthosporium, above all against *Helminthosporium gramineum*, the pathogen of stripe disease of barley. It can therefore be used especially for the treatment of seed (seed dressing).

The active compound which can be used according to the invention is well tolerated by plants. It has only a low toxicity to warm-blooded animals and because of its lack of odor and its good toleration by human skin it is not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, bird repellents, plant nutrients, agents for improving soil structure, etc. if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In the treatment of seed, amounts of active compound of 0.01 to 50 g per kilogram of seed, preferably 0.5 to 5 g, are generally required.

Furthermore, the present invention contemplates methods of selectively killing, combating or controlling pests, e.g. fungi of the genus Helminthosporium, which comprises applying to at least one of correspondingly (a) such fungi, and (b) the corresponding habitat thereof, i.e. the locus to be protected, e.g. to a growing crop, to an area where a crop is to be grown, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular compound of the present invention are illustrated, without limitation, by the following examples:

EXAMPLE 1

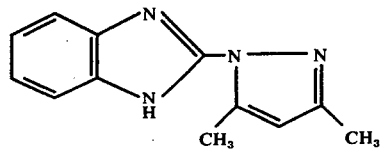

(I)

888 g (6 moles) of 2-hydrazino-benzimidazole were dissolved in 6.6 l of 2 N hydrochloric acid at 40° C, while stirring. 720 g (7.2 moles) of acetylacetone were added all at once. A precipitate soon separated out. After the reaction had subsided, the mixture was additionally warmed to a temperature of 80° C over the course of 3 hours and was then allowed to cool to 65° C, 2.4 l of methanol were added and the mixture was neutralized by adding crystalline sodium carbonate. The reaction product which had precipitated was filtered off, washed with water and pressed out. The melting point of the crude product was 130°–132° C. It was purified by warming in a mixture of 9 l of water and 550 ml of concentrated hydrochloric acid, while stirring, until it had dissolved, clarifying the solution with animal charcoal, adding 3 l of methanol and neutralizing the mixture with crystalline sodium carbonate, whereupon the product precipitated. The product was isolated as described above and dried at a temperature of 80° C until constant weigh had been reached. 1,150 g (that is to say 90% of theory) of 2-[3′,5′-dimethyl-pyrazolyl-(1′)]-benzimidazole of melting point 133.5°–135° C were obtained.

EXAMPLE 2

Seed dressing test/stripe disease of barley(seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, on moist filter paper discs in closed Petri dishes, was exposed to a temperature of 4° C for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18° C in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentration of the active compounds in the dressing, the amounts of dressing used and the number of diseased plants can be seen from the following table:

Table 1
Seed dressing test/stripe disease of barley
| Active compound | | Active compound concentration in the dressing in % by weight | Amount of dressing used in g/kg of seed | Number of plants with stripe disease in % of the total emerged plants |
|---|---|---|---|---|
| Without dressing | | — | — | 52.5 |
| Known comparison compounds: | | | | |
| 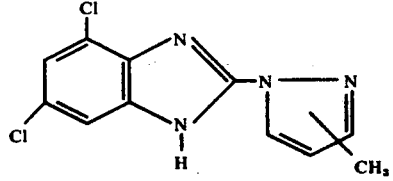 | (A) | 30 | 2 | 47.9 |
| 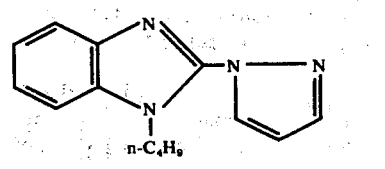 | (B) | 30 | 2 | 19.6 |
| 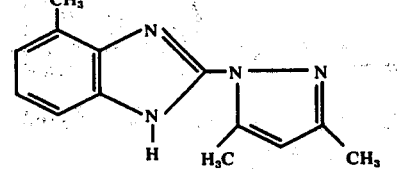 | (C) | 30 | 2 | 41.8 |
| 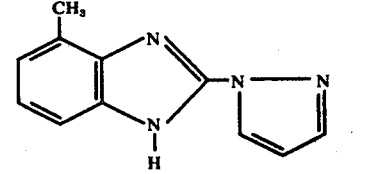 | (D) | 30 | 2 | 16.9 |
| 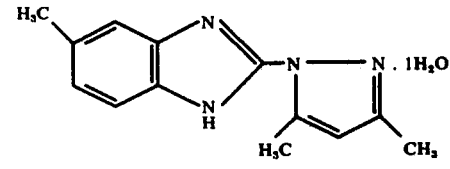 | (E) | 30 | 2 | 40.8 |
| 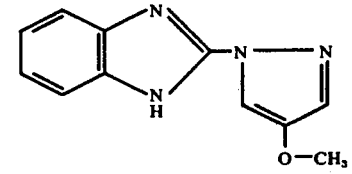 | (F) | 30 | 2 | 37.4 |
| 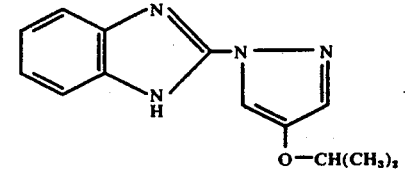 | (G) | 30 | 2 | 20.9 |
| 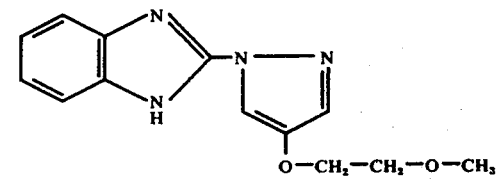 | (H) | 30 | 2 | 36.4 |
According to the invention:

Table 1-continued

| Active compound | Seed dressing test/stripe disease of barley | | | |
|---|---|---|---|---|
| | | Active compound concentration in the dressing in % by weight | Amount of dressing used in g/kg of seed | Number of plants with stripe disease in % of the total emerged plants |
| 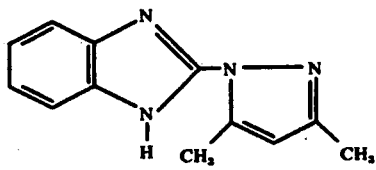 | (I) | 30 | 2 | 0.0 |
| | | 10 | 3 | 3.1 |

It will be appreciated that the instant specification and examples are set forth by way of illustration and not limitation, and that various modifications and changes may be made without departing from the spirit and scope of the present invention.

What is claimed is:

1. A method of combating fungi from the genus Helminthosporium which comprises applying to such fungi a fungicidally effective amount of 2-[3',5'-dimethyl-pyrazolyl-(1')]-benzimidazole of the formula 2. A method according to claim 1, in which the 2-[3',5'-dimethylpyrazolyl-(1')]-benzimidazole is applied to seed.

3. A method according to claim 2, in which the 2-[3',5'-dimethylpyrazolyl-(1')]-benzimidazole is applied in an amount of from 0.01 to 50 g per kilogram of seed.

4. A method according to claim 2, in which the 2-[3',5'-dimethylpyrazolyl-(1')]-benzimidazole is applied in an amount of from 0.5 to 5 g per kilogram of seed.

5. A method according to claim 1, in which the fungus is *Helminthosporium gramineum*.

* * * * *